United States Patent [19]

Nowacki et al.

[11] Patent Number: 5,056,917
[45] Date of Patent: Oct. 15, 1991

[54] LITHOTRIPTER REFLECTOR INSPECTION

[76] Inventors: Christopher Nowacki, 1552 Chickamauga, Long Grove, Ill. 60047; Mark T. Horbal, 2 S. 530 Iroquois Cts. West, Warrenville, Ill. 60555

[21] Appl. No.: 502,802

[22] Filed: Apr. 2, 1990

[51] Int. Cl.$^5$ ............................ G01B 9/00; A61H 1/00
[52] U.S. Cl. ............................. 356/124; 128/24 EL; 606/2
[58] Field of Search ............... 356/124, 125, 126, 127; 128/24 AA, 328, 660.03, 24 EL; 600/15; 606/2, 13

[56] References Cited

U.S. PATENT DOCUMENTS

| | | | |
|---|---|---|---|
| 4,930,509 | 6/1990 | Brisson | 128/653 |
| 4,932,954 | 6/1990 | Wondrazek et al. | 606/128 |
| 4,966,132 | 10/1990 | Nowacki et al. | 128/24 A |

OTHER PUBLICATIONS

Webster's New World Dictionary, Neufeldt et al, 1988, p. 997.

*Primary Examiner*—F. L. Evans
*Assistant Examiner*—K. P. Hantis

[57] ABSTRACT

Structure is provided for inspecting a lithotripter ellipsoidal reflector. In one form of the invention a narrow light beam such as a laser light beam is projected through the first focus point of the reflector as relfects on to a target on the axis of reflection, thereby indicating visually the location of the second focus point. The target preferably is a rod lying on the axis of rotation. Preferably the light source is movable in a vertical plane, and the reflector is rotatable about its axis of rotation to provide redundancy in location of the second focus point. In a further form of the invention the target comprises a photocell so that the accuracy and reflectivity of the reflecting surface can be measured.

20 Claims, 1 Drawing Sheet

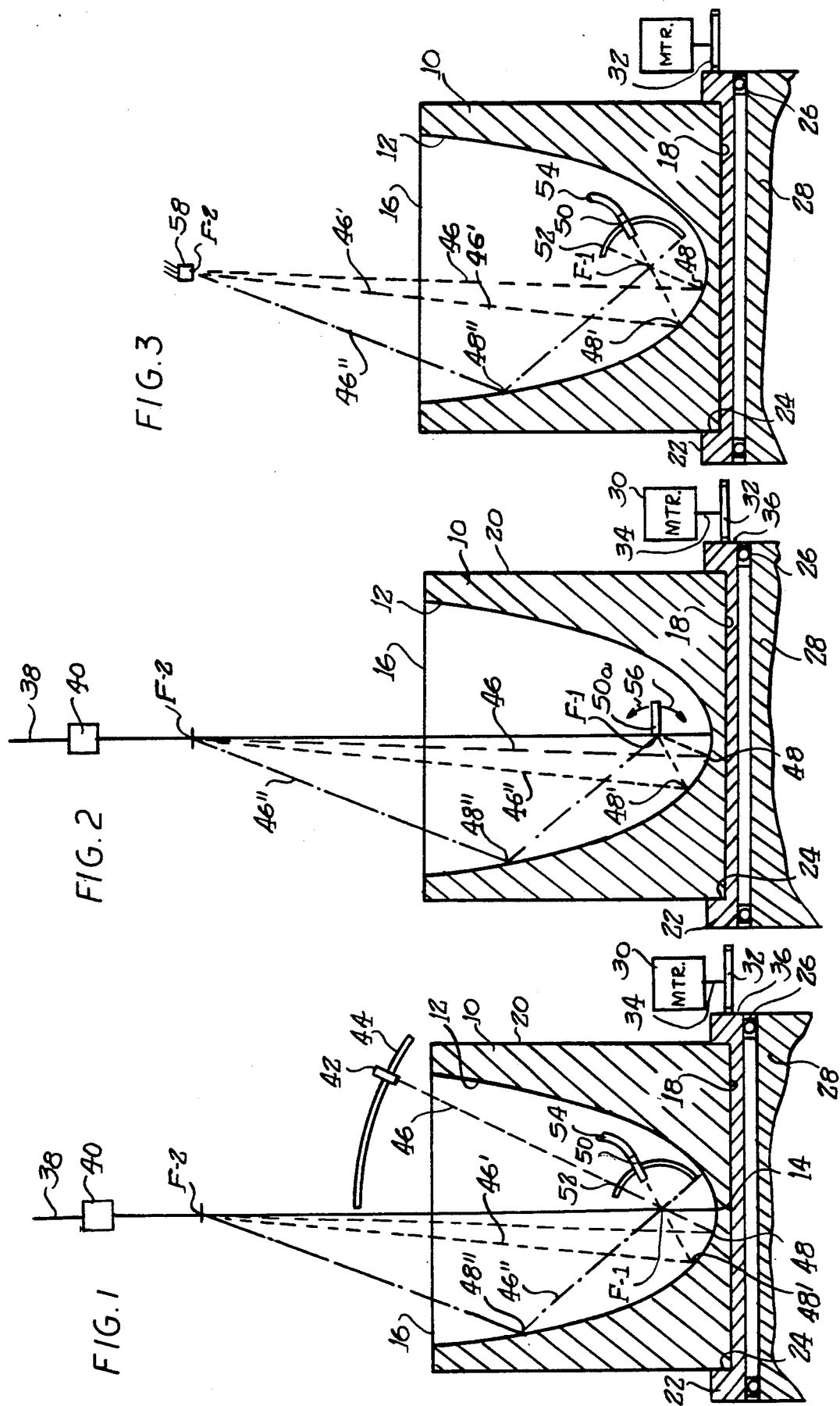

LITHOTRIPTER REFLECTOR INSPECTION

BACKGROUND OF THE INVENTION

Lithotripters for use in the extracorporeal destruction of kidney stones have become well known. Such devices use a reflector that is a portion of an ellipsoid. A spark generating device is positioned at the first focus point of the ellipsoid, while the ellipsoid is truncated so that the second focus point can be located precisely on the kidney stone, gallstone, or other concretion to be disintegrated. As is known, the reflector is filled with water, and is coupled to the body containing the concretion that is to be disintegrated. The spark gap previously noted has a series of sparks jump across it under water. This causes flashing of some of the water into steam, some dissociation of the water, and generally creates a shockwave which is reflected by the truncated ellipsoidal reflector. The shockwave passes through the water in the reflector and through the human body, which is mostly water and focuses on the stone which in due course is reduced to dust which passes out with the urine. The process is also useful in destroying concretions in the gall bladder.

The first focus point is relatively easily located, either by calculations, or by the predetermined position of the spark gap. However, it is difficult to ascertain simply and with accuracy the location of the second focus point. Furthermore, it is difficult to test the ellipsoidal reflector surface to make sure that it is substantially perfect, and within tolerances.

OBJECTS AND SUMMARY OF THE PRESENT INVENTION

It is an object of the present invention to provide structure for simple and positive precise location of the second focus point of the ellipsoidal reflector of a lithotripter device.

It is a further object of the invention to provide such structure which also can be used for testing the surface of the ellipsoidal reflector to insure that it has been manufactured within tolerances.

In attaining the foregoing and other objects of the present invention we mount the ellipsoidal reflection on a precision turntable so that it can be rotated through 360° about its own axis. A laser or other very narrow beam of light is projected through the first focus point of the reflector. The position of the beam is varied in a vertical plane so as to pass through the first focus point in every direction that can have a reflection. The reflected light is focused on a vertical transparent or translucent rod or the like for display of the position of the second focus point. When the focus point has been precisely located a photocell can be positioned at the second focus point, and the light beam again can be passed through the first focus point for reflection to the photocell at the second point. Assuming that the reflector is of the type having a highly polished surface the photocell will accurately measure precisely how much light is reflected. Ideally, there should be a constant level of light received by the photocell, and variations in the light level will indicate deviations from perfection of the reflector surface.

THE DRAWINGS

The present invention will best be understood from the following description when taken in connection with the drawings wherein:

FIG. 1 is a somewhat schematic axial sectional view through a lithotripter ellipsoidal reflector under test, and the structure supporting the reflector;

FIG. 2 is a view similar to FIG. 1 showing a modification of the structure of the invention; and FIG. 3 is a view similar to FIGS. 1 and 2 with a photocell in place for testing perfection of the reflective surface.

DETAILED DISCLOSURE OF THE ILLUSTRATED EMBODIMENTS

Reference first should be had to FIG. 1 wherein there is shown a lithotripter ellipsoidal reflector block 10 having an ellipsoidal reflecting surface 12. This may be a polished surface. The reflector surface 12 has an apex at 14 and opens upwardly at the upper end at 16. In the illustrative example the bottom of the block 10 is flat at 18, and the outer surface 20 is cylindrical, although these shapes are not essential. The block is received in a turntable 22 having a recess 24 in which the block is seated. The turntable 22 is supported by ball bearings 26 on an underlying support structure 28. A motor 30 has a gear 32 mounted on the motor shaft 34 engaging the outer edge 36 of the turntable. The outer edge 36 may have gear teeth, or it may be serrated. Alternatively, the gear can simply be a wheel 22 with a rubber tire or the like frictionally driving the outer cylindrical edge 36 of the turntable 22.

A transparent rod 38 of glass or plastic is supported by a fixture 40 coincident with the axis of rotation of the reflector surface 12 and extending through the first focus point F-1 to the apex 14. The rod may be completely transparent, or it may be lightly translucent or colored. A laser light source 42 is supported above the open top 16 of the reflector and is supported as on an arcuate track 44 on which it is movable by any suitable known means. It may be moved manually, or it may be motor driven. The light emitting device 42 can use a very fine or well focused beam of light other than laser, but laser is exemplary. The light beam 46 is projected through the first focus point F-1, and impinges against the reflector 12 at 48, and is reflected up to the second focus point F-2 where it can be seen engaging the rod. In the illustrative example the arcuate track 44 comprises a circular arc about the first focus point F-1 as a center. However, it will be appreciated that more complicated arrangements could be used so that the light source 42 could be moved from left to right (or vice versa) as seen in FIG. 1, and oriented so that it would at all times have the light beam 46 projecting through the first focus point F-1.

A point is reached at which the light source 42 cannot move further to the right without having the light beam engage the top edge of the reflector, thus shadowing the focus point F-1 so that the light beam could not strike it. Accordingly, a secondary light source 50 is positioned within the reflector and near the focus point F-1. The secondary light source 50 is movable on an arcuate track 52 which comprises an arc about the focus point F-1 as a center. The light source 50 may be a small laser light source directly on the arc, or it may be the exit point of a fiber optic bundle 54 connected to a laser or other light source outside the reflector. In any event, the light source 50 can be moved along the arc 52, always projecting through the first focus point. With the secondary light source 50 in the position shown in FIG. 1, the light beam 46' reflects from the reflector surface 12 at 48' and again engages the rod 38 at the second focus point F-2. Similarly, with the secondary light source 50 shifted to a position near the bottom of the arc 52, the light beam 46" will reflect from a point 48" on the reflector wall, and again up to the second focus point F-2.

It will be observed that the primary light source 42 can be omitted if a suitable range of movement is imparted to the secondary light source 50. In any event, as the light source is shifted in a vertical plane to intersect the focus point F-1 from different source positions, the light beam will be reflected up to the second focus point F-2. The light beam will illuminate the rod 38 where it engages the rod, thereby identifying a second focus point F-2. The rod may have, and preferably does have, marking indicia thereon (not shown) so that the precise position of the second focus point F-2 from the apex 14 may be read easily. In addition to moving the light source 42 and/or 50 in a vertical plane, the motor 30 causes the entire reflector block 10 to rotate in a horizontal plane, whereby the second focus point F-2 can be checked from many reflector points on the wall of the reflector surface 12, to get a most accurate positioning of the second focus point F-2.

The parts and the arrangement thereof in FIG. 2 are mostly the same as in FIG. 1, and similar numerals are utilized to identify similar parts to avoid the necessity of duplication of description. The essential difference is that there is a single light source of laser light or the like 50a which is supported at the focus point F-1, and which is pivotable up and down about this pivot point as indicated by the arcuate arrows 56. The same results are produced as with FIG. 1 in that there is a very large number of light paths through the first focus point F-1 that are reflected up to the second focus point F-2 for accurate location of the second focus point. Again, the turntable 22 is rotated by the motor 30 to cause reflection from all parts of the reflector surface 12 just as in FIG. 1.

The parts and arrangements of parts in FIG. 3 again are for the most part the same as in FIG. 1, and again the numerals are used for the same parts to avoid prolixity of description. The essential difference is that the rod 38 is omitted, and a sensitive photocell 58 is mounted in fixed position with its receptor surface precisely at the second focus point F-2. The light 50 again is moved along the arcuate track 52, and the turntable 22 is turned to cause the reflecting surface 12 to turn about its rotational axis. The reflective surface is highly polished, and if the surface is perfect, the light as measured by the photocell 58 will be constant regardless of the position of the light source 50 and of the position of rotation of the reflector block 10. This allows the reflector surface 12 to be measured with great accuracy.

It will now be apparent that we have disclosed structure and method for accurately determining the second focus point of a truncated ellipsoidal reflector for use in a lithotripter. We have also disclosed structure and a method for measuring the intensity of light reflected from the surface of the ellipsoidal reflector, thereby providing an indication of the perfection of location and reflectivity of the reflector surface.

The transparent or translucent rod 38 and the photocell 58 both may be regarded as targets in that the reflected light is intended to strike at the F-2 focus point location. It will be appreciated that the focus point F-2 can be found by a single light beam through the first focus point and reflected from the wall. When the light source is moved in a vertical plane, and the reflector is rotated about its rotational axis, as disclosed, there is a great deal of redundancy which provides greater accuracy in determining the second focus point F-2.

The specific examples as herein shown and described will be understood as being for illustrative purposes. Various changes in structure will no doubt occur to those skilled in the art, and will be understood as forming a part of the present invention insofar as they fall within the spirit and scope of the appended claims.

The invention is claimed as follows:

1. The combination comprising a truncated ellipsoidal reflector having a truncated reflecting surface having an axis of rotation and an apex and a first focus point on said axis of rotation, there being a second focus point disposed on said axis of rotation outside said truncated ellipsoidal reflector, and structure for inspecting said reflector, comprising support means for said reflector, a source of a narrow beam of light movable relative to said reflector to project through said first focus point and to reflect from said reflecting surface, a target substantially at said second focus point for engagement by said reflected light beam, and means for moving said light beam source relative to said reflector while projecting said light beam through said first focus point to reflect from a successive plurality of areas of said reflecting surface.

2. The combination as set forth in claim 1 and further including means mounting said light source for movement in a vertical plane and projecting said light beam through said first focus point from a plurality of different positions.

3. The combination as set forth in claim 2 wherein the mounting means for said light source is disposed outside of said truncated reflector.

4. The combination as set forth in claim 2 wherein said light source is disposed inside said truncated reflector.

5. The combination as set forth in claim 2 and further including two light sources, and means for mounting one of said light sources outside of said truncated reflector, and means for mounting the other said light sources inside said truncated reflector.

6. The combination as set forth in claim 1 wherein said support means includes means for rotating said reflector about said axis of rotation.

7. The combination as set forth in claim 6 and further including means mounting said light source for movement in a vertical plane and projecting said light beam through said first focus point from a plurality of different positions.

8. The combination as set forth in claim 6 wherein the mounting means for said light source is disposed outside of said truncated reflector.

9. The combination as set forth in claim 6 wherein said light source is disposed inside said truncated reflector.

10. The combination as set forth in claim 6 and further including two light sources, and means for mounting one of said light sources outside of said truncated reflector, and means for mounting the other of said light sources inside said truncated reflector.

11. The combination as set forth in claim 1 wherein said target lies on said axis of rotation for visually displaying the location of the second focus point where said reflected light beam engages said target.

12. The combination as set forth in claim 11 wherein said target is pellucid.

13. The combination as set forth in claim 12 wherein said target is transparent.

14. The combination as set forth in claim 12 wherein said target is translucent.

15. The combination as set forth in claim 11 wherein said target comprises a rod.

16. The combination as set forth in claim 15 wherein said rod is pellucid.

17. The combination as set forth in claim 11 and further including means mounting said light source for movement in a vertical plane and projecting said light beam through said first focus point from a plurality of different positions.

18. The combination as set forth in claim 11 wherein said support means includes means for rotating said reflector about said axis of rotation.

19. The combination as set forth in claim 17 wherein said support means includes means for rotating said reflector about said axis of rotation.

20. The combination as set forth in claim 1 wherein said target comprises photosensitive means for measuring the accuracy and reflectivity of said reflecting surface.

* * * * *